United States Patent
Yarger

(10) Patent No.: US 7,776,004 B2
(45) Date of Patent: *Aug. 17, 2010

(54) ASPIRATOR SLEEVE AND SUCTION HANDLE

(75) Inventor: Richard J. Yarger, Yakima, WA (US)

(73) Assignee: Surgimark, Inc., Yakima, WA (US)

( * ) Notice: Subject to any disclaimer, the term of this patent is extended or adjusted under 35 U.S.C. 154(b) by 553 days.

This patent is subject to a terminal disclaimer.

(21) Appl. No.: 11/736,396

(22) Filed: Apr. 17, 2007

(65) Prior Publication Data

US 2007/0203449 A1    Aug. 30, 2007

Related U.S. Application Data

(63) Continuation-in-part of application No. 11/405,270, filed on Apr. 17, 2006, which is a continuation-in-part of application No. 10/969,276, filed on Oct. 19, 2004, now Pat. No. 7,066,903, which is a continuation of application No. 10/153,420, filed on May 22, 2002, now abandoned.

(51) Int. Cl.
*A61M 1/00* (2006.01)
*A61M 25/00* (2006.01)

(52) U.S. Cl. .................. 604/35; 604/118; 604/268

(58) Field of Classification Search .............. 604/6.16, 604/19, 35, 43–45, 48, 129, 242–243, 263–264, 604/513, 533, 540–542, 266; 433/91
See application file for complete search history.

(56) References Cited

U.S. PATENT DOCUMENTS

| 1,388,312 A | 8/1921 | Seeger |
| 2,220,493 A | 11/1940 | Pixler |
| 3,308,825 A | 3/1967 | Cruse |
| 3,416,532 A | 12/1968 | Grossman |
| 3,528,427 A | 9/1970 | Sheridan |

(Continued)

FOREIGN PATENT DOCUMENTS

| EP | 0 457 220 A1 | 11/1991 |
| EP | 1 364 665 A1 | 11/2003 |
| FR | 2.170.858 A | 9/1973 |
| GB | 1 531 416 A | 11/1978 |
| WO | 96/04950 A1 | 2/1996 |

OTHER PUBLICATIONS

EPO Communication dated Sep. 22, 2003, issued in corresponding European Application No. 03445061.9, filed May 20, 2003.

(Continued)

*Primary Examiner*—Kevin C Sirmons
*Assistant Examiner*—Andrew M Gilbert
(74) *Attorney, Agent, or Firm*—Christensen O'Connor Johnson Kindness PLLC

(57) ABSTRACT

A surgical aspirator tip and sleeve combination includes a hollow aspirator tip adapted to be placed into communication with a suction source, a grip portion, a coupling portion extending distally from the grip portion, and a neck portion extending distally from the coupling portion. The surgical aspirator sleeve is receivable on the tip to define an internal channel between the sleeve and the neck portion. The internal channel is in fluid communication with the interior of the tip. A plurality of spaced orifices on the sleeve provide communication between the external environment and the internal channel. At least one longitudinal groove is formed at least partially within the grip portion and the coupling portion. The longitudinal groove defines a venting channel in communication with the internal channel and the external environment. The longitudinal groove is adapted to be at least partially covered to adjust the suction within the internal channel.

14 Claims, 15 Drawing Sheets

U.S. PATENT DOCUMENTS

| | | | |
|---|---|---|---|
| 3,965,901 A * | 6/1976 | Penny et al. | 604/119 |
| 4,398,910 A | 8/1983 | Blake | |
| 4,465,481 A | 8/1984 | Blake | |
| 4,490,138 A | 12/1984 | Lipsky | |
| 4,648,871 A | 3/1987 | Jacob | |
| 4,662,871 A | 5/1987 | Rafelson | |
| 4,767,404 A | 8/1988 | Renton | |
| 4,867,747 A | 9/1989 | Yarger | |
| 5,024,615 A | 6/1991 | Büchel | |
| 5,360,414 A | 11/1994 | Yarger | |
| 5,690,487 A | 11/1997 | Whitehouse | |
| 5,817,050 A | 10/1998 | Klein | |
| 5,890,516 A * | 4/1999 | Talamonti | 137/605 |
| 5,899,884 A * | 5/1999 | Cover et al. | 604/119 |
| 5,921,999 A | 7/1999 | Dileo | |
| 7,066,903 B2 * | 6/2006 | Yarger | 604/35 |
| 2001/0002432 A1 | 5/2001 | Bugge | |

OTHER PUBLICATIONS

EPO Communication dated Aug. 31, 2004, issued in corresponding European Application No. 03445061.9, filed May 20, 2003.
EPO Communication dated Sep. 28, 2005, issued in corresponding European Application No. 03445061.9, filed May 20, 2003.

* cited by examiner

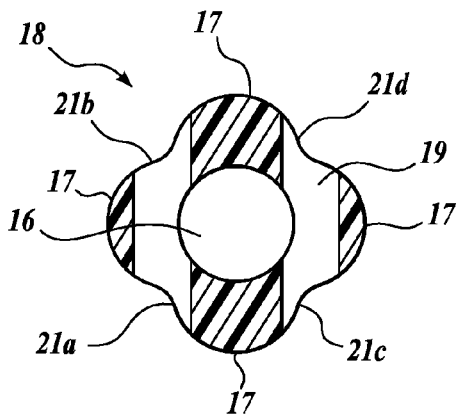
Fig.3B.
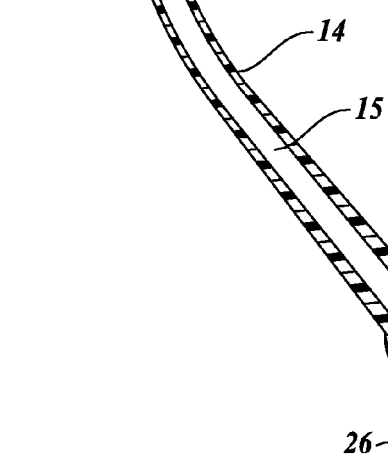
Fig.3A.
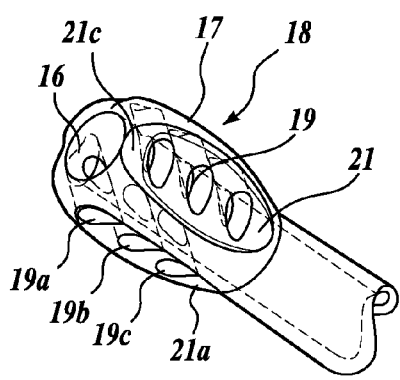
Fig.3C.
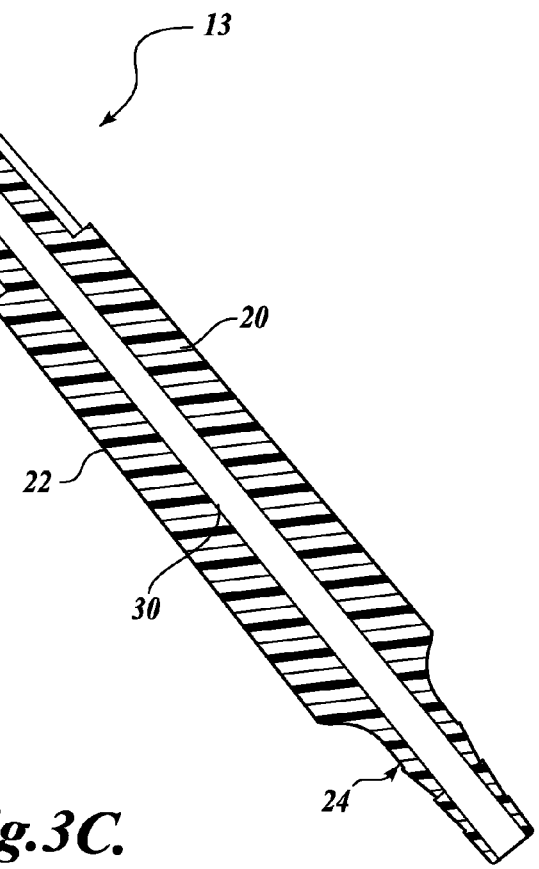

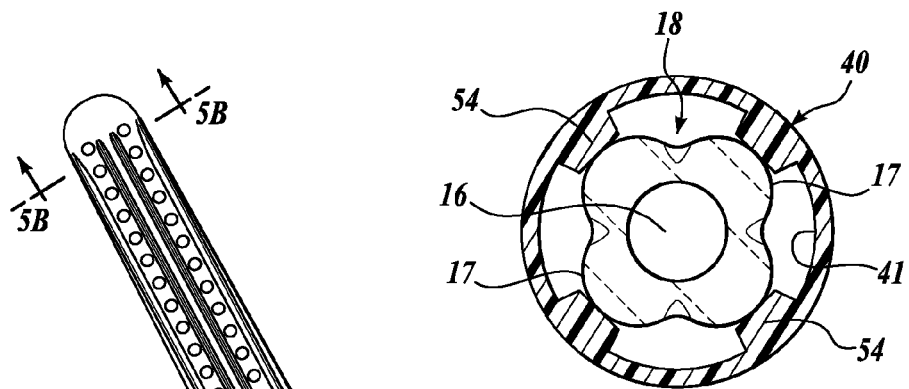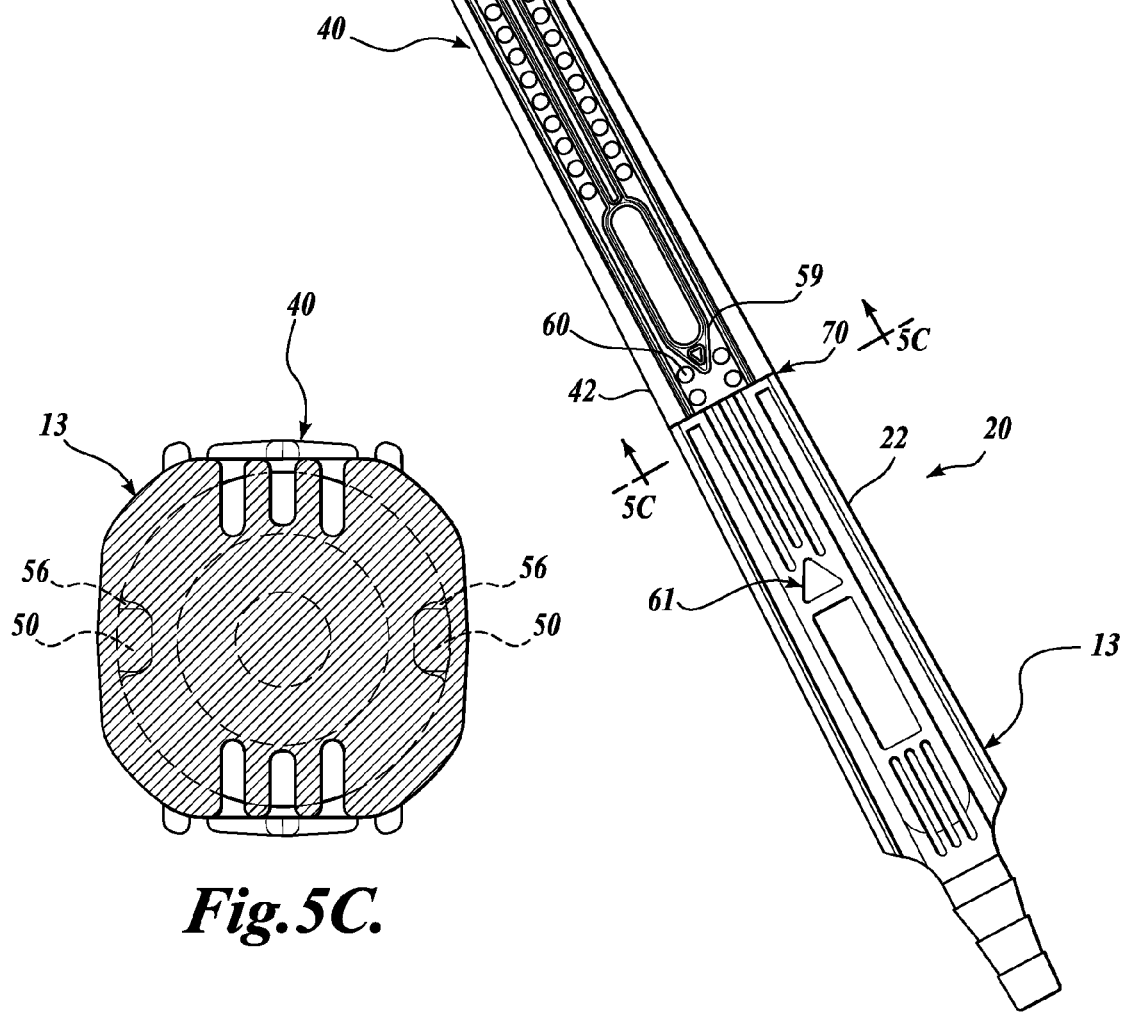

ASPIRATOR SLEEVE AND SUCTION HANDLE

CROSS-REFERENCES TO RELATED APPLICATIONS

This application is a continuation-in-part of prior U.S. patent application Ser. No. 11/405,270, filed Apr. 17, 2006, which is a continuation-in-part of U.S. patent application Ser. No. 10/969,276, filed Oct. 19, 2004, now U.S. Pat. No. 7,066,903, which is a continuation of application Ser. No. 10/153,420, filed May 22, 2002, now abandoned, the specification of which are hereby incorporated.

BACKGROUND

Surgical aspirators are used to remove fluids from the body of the patient. A surgical aspirator typically includes a tip that is inserted into a surgical site, wound, or other bodily orifice. The tip is generally elongated in shape and may include a handle or grip section to facilitate using and holding the aspirator. The proximal end of the tip is connected to a tube that is connected to a suction pump that provides suction to the tip. The distal end of the aspirator tip is inserted into the patient and has one or more openings into which gases, fluids, and materials may flow.

Pieces of tissue and other debris may be suspended in the fluids and can clog the aspirator tip. Thus, the distal end of the aspirator tip may be covered with a sleeve that is formed with a plurality of small holes. The holes prevent the tissue from reaching the opening of the aspirator tip while allowing the fluid being evacuated to flow into the sleeve through the holes.

This action could be further enhanced by using internal projections defined on the interior surface of the sleeve to maintain the position of the sleeve relative to the aspirator tip. Projections may also be used to ensure adequate space between the aspirator tip and the sleeve. Therefore, fluids and small debris may flow freely to or through the aspirator tip end opening.

Venting channels may additionally be formed between the sleeve and tip to sustain uniform distribution of suction in the event that the holes in the sleeve become clogged. The venting channels should be properly aligned with the sleeve to ensure that airflow reaches the interior of the sleeve if any of the holes become clogged. Without such airflow, suction will no longer be uniformly distributed among the unclogged holes. This may result in excess suction in particular areas of the sleeve that may pull surrounding tissue, thereby causing injury to the patient. It would be beneficial to use a sleeve locking mechanism to secure the position of the sleeve relative to the aspirator tip such that the venting channels are maintained between the sleeve and tip during use.

Based on the foregoing, a need exists for an improved surgical aspirator tip and sleeve combination that allows air flow into the interior of the sleeve and towards the tip end opening and through properly aligned venting channels existing between the sleeve and tip. A need also exists for an improved surgical aspirator tip and sleeve combination that enables a user to vary the level of suction within the sleeve to safely and efficiently drain fluids from a body cavity.

SUMMARY

A surgical aspirator tip and sleeve combination constructed in accordance with one embodiment of the present disclosure is depicted. The surgical aspirator tip includes a hollow interior that is adapted to be placed into communication with a suction source, a grip portion, a coupling portion extending distally from the grip portion, and a neck portion extending distally from the coupling portion. The surgical aspirator sleeve is slidably receivable on the surgical aspirator tip to define an internal channel between the aspirator sleeve and the neck portion of the surgical aspirator tip, wherein the internal channel is in fluid communication with the hollow interior of the aspirator tip, and wherein the aspirator sleeve includes a plurality of spaced orifices that provide fluid communication between the external environment and the internal channel. The surgical aspirator tip includes at least one longitudinal groove formed at least partially within the grip portion and the coupling portion, wherein the longitudinal groove defines a venting channel in communication with the internal channel and the external environment. The longitudinal groove is adapted to be at least partially covered to adjust the suction within the internal channel.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

The foregoing aspects and many of the attendant advantages of this invention will become more readily appreciated as the same become better understood by reference to the following detailed description, when taken in conjunction with the accompanying drawings, wherein:

FIG. 3A is a longitudinal cross-section view of the surgical aspirator tip of FIG. 1;

FIG. 3B is a cross-section view of a surgical aspirator tip end of the surgical aspirator tip of FIG. 2, taken across 3B-3B;

FIG. 3C is a side perspective view of the surgical aspirator tip end of FIG. 2;

FIG. 5A is a front view of a surgical aspirator tip joined with a surgical aspirator sleeve;

FIG. 5B is a cross-section view of the surgical aspirator tip end engaging the sleeve tip end projections, taken across 5B-5B;

FIG. 5C is a cross-section view of the surgical aspirator tip engaging the surgical aspirator sleeve, taken across 5C-5C;

DETAILED DESCRIPTION

Embodiments of a surgical aspirator tip and sleeve combination will now be described with reference to the drawings where like numerals correspond to like elements. Although embodiments of the present disclosure will be depicted generally as Yankauer or Andrews aspirator tips, one skilled in the relevant art will appreciate that the disclosed embodiments are illustrative in nature, and therefore, should not be construed as limited to application with either a Yankauer or Andrews tip. It should therefore be apparent that the embodiments of the present disclosure have wide application, and may be used on any similar aspirator tip and sleeve combination, such as a Frazier aspirator tip and sleeve combination. Accordingly, the following descriptions and illustrations herein should be considered illustrative in nature, and not limiting the scope of the present disclosure, as claimed.

Figure 1:
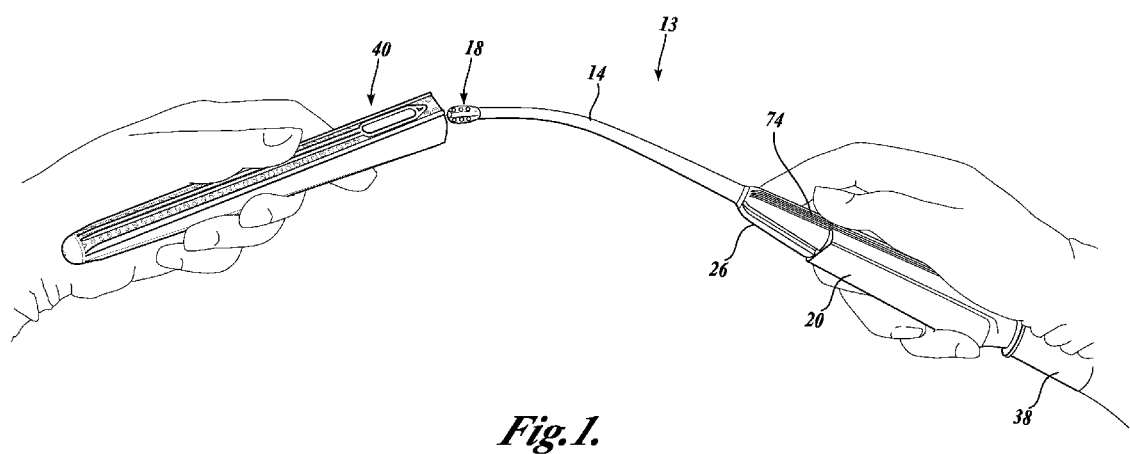
FIG. 1 is a side elevational view of a surgical aspirator tip and a surgical aspirator sleeve.

FIGS. 1-5 depict an embodiment of a surgical aspirator tip and sleeve combination. FIG. 1 shows a surgical aspirator tip 13, which may be received into a surgical aspirator sleeve 40 to form the surgical aspirator tip and sleeve combination.

Figure 2:
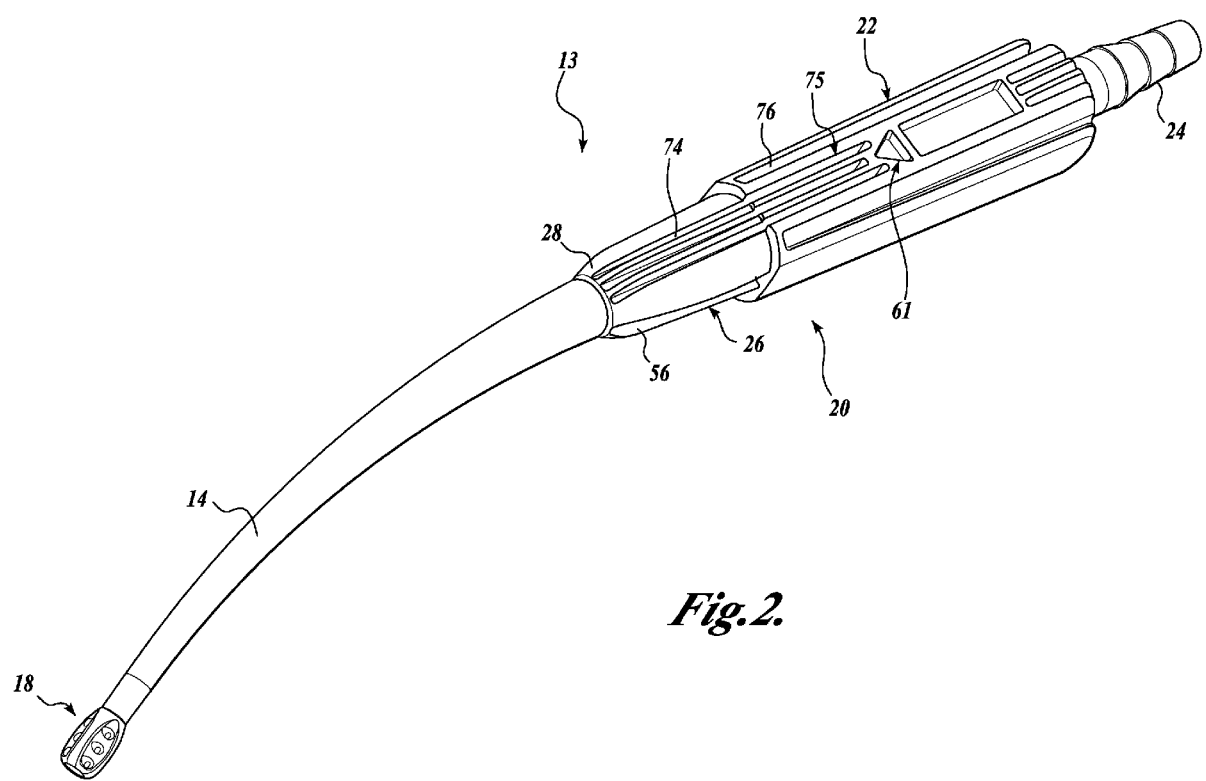
FIG. 2 is a side elevational view of the surgical aspirator tip of FIG. 1.

FIG. 2 depicts the surgical aspirator tip 13. The tip 13 generally includes a hollow tubular neck portion, or member 14 that is inserted into the wound, bodily orifice, or surgical site, and an enlarged hollow medial section, or elongated handle member 20. The handle member 20 includes a grip portion or member 22 for gripping the tip 13, a tube coupling member 24 that is used to attach the tip 13 to a tube 38 (depicted in FIG. 1) that in turn is connected to a source of suction (not shown), and a male coupling portion, or a male coupling member 26 for attaching a sleeve 40 (see FIG. 1) to the tip 13. The handle member 20 and tubular neck member 14 are constructed from a rigid or semi-rigid, resiliently deformable material that is adaptable for use in the medical arts. Preferably, polymeric or resinous plastic is used.

FIG. 3A depicts a cross-sectional view of the surgical aspirator tip 13. The handle member 20 defines a longitudinal internal channel 30. The proximal end of the tubular neck member 14 is attached to the distal end of the handle member 20 so that the interior 15 of the tubular neck member 14 is in communication with the internal channel 30 in the handle member 20.

As shown in FIGS. 3A-3C, an enlarged tip end portion 18, open at its distal end, is formed on the distal end of the tubular neck member 14. The tip end portion 18 defines a tip end opening or orifice 16 into which gases, fluids, and materials can flow. The tip end portion 18 is formed with tip end projections or ridges 17 that extend along the tip end portion 18. The tip end ridges 17 form tip end grooves 21 therebetween. The tip end portion 18 is preferably formed with four tip end ridges 17 that are generally the same size and shape and equidistant from one another, each ridge 17 being diametrically opposite another ridge 17. The tip end ridges 17 are used to abut the sleeve 40 to form a gap between the tip end portion 18 and the sleeve 40. However, if the tip 13 is used without the sleeve 40, the tip end ridges 17 are capable of bridging the adjacent soft tissue and maintaining the channels in the grooves 21 open for the flow of fluid, gas, and materials through the channels.

The tip end portion 18 may include additional tip end apertures or orifices 19. The tip end apertures 19 are formed in tip end grooves 21, and each tip end aperture 19 extends laterally through the tip end portion from a first tip end groove 21 to an adjacent tip end groove 21. FIGS. 3A-3C illustrate three rows of tip end apertures 19a-19c formed between adjacent tip end grooves 21a and 21b, and three rows of tip end apertures 19a-19c formed between adjacent tip end grooves 21c and 21d. Each row of tip end apertures 19a-19c is positioned substantially parallel to the other rows. The tip end apertures 19 intersect the tip end opening 16, such that the tip end apertures 19 are in communication with the tip end opening 16. In this manner, gases, fluids, and materials may flow within the grooves 21, through the tip end orifices 19, and into the opening 16 in the distal end of the neck portion 14. Although 3 rows of apertures are shown, it is to be understood that other numbers of rows of apertures 19, either fewer or greater in number, can be utilized. Also, the apertures are shown as round in cross-section, but the apertures can be of other cross-sectional shapes, such as oval, hexagonal, octagonal, etc.

Figure 4A:
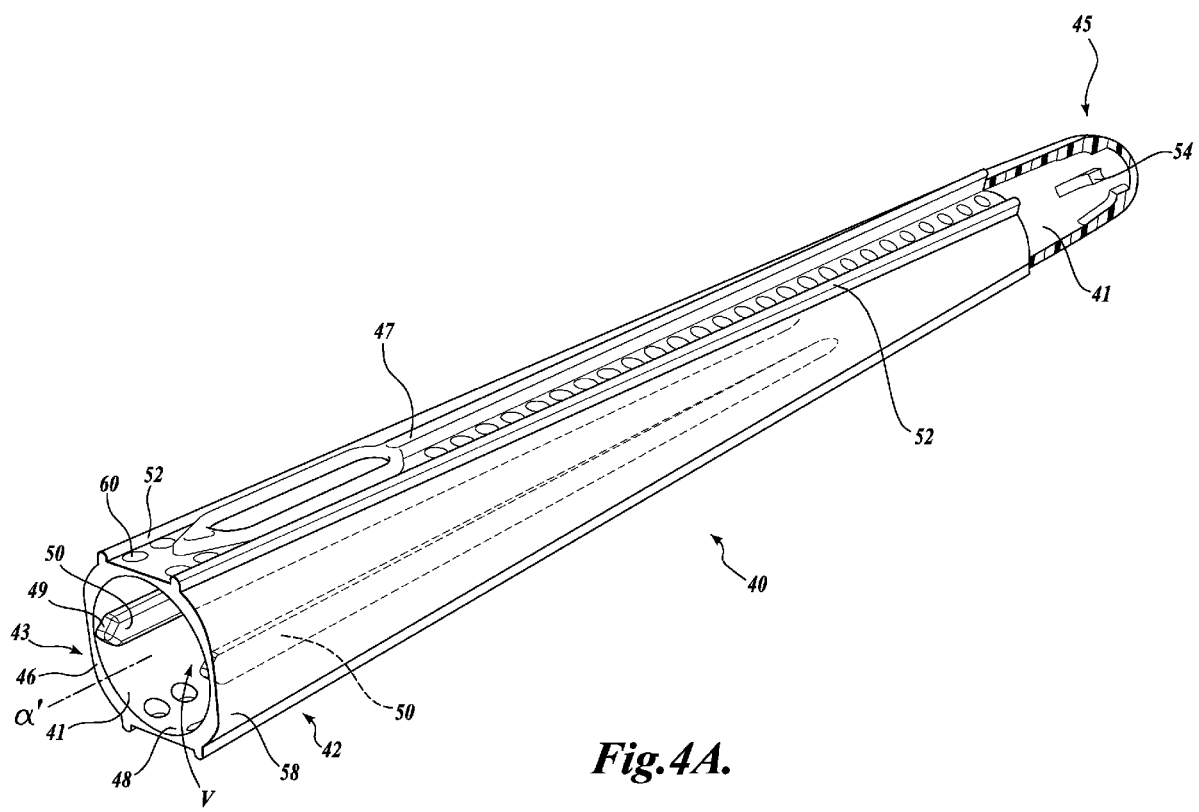
FIG. 4A is a side perspective view of a surgical aspirator sleeve, where the sleeve is cut away to show the interior ribs and sleeve tip end projections.
Figure 4B:
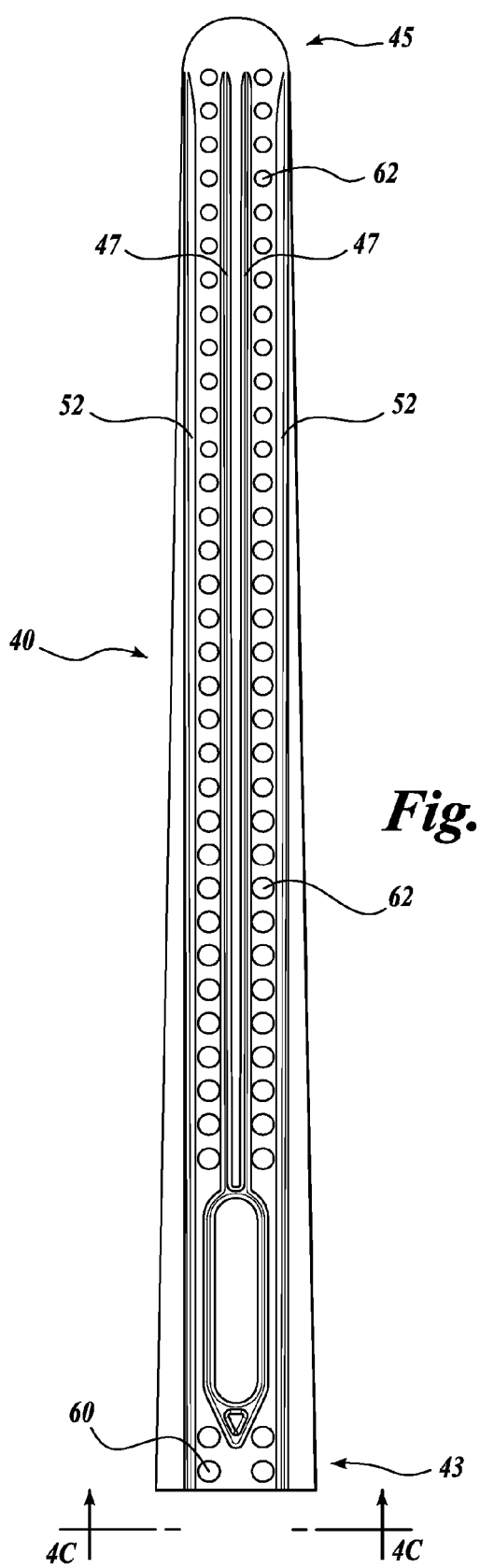
FIG. 4B is a front view of a surgical aspirator sleeve.
Figure 4C:
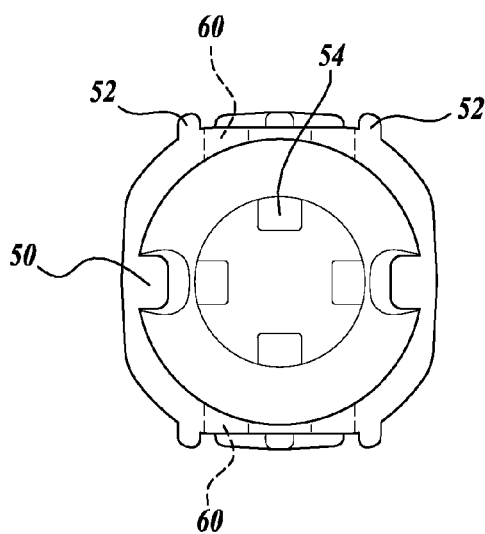
FIG. 4C is an end view of the surgical aspirator sleeve.

Now referring to FIGS. 4A, 4C, 5B, and sleeve 40 may include sleeve tip end projections 54 that protrude from the interior surface of the sleeve 41 at the distal tip sleeve end portion 45. Four sleeve tip projections 54 are shown as formed and configured to abut the four tip end ridges 17 when the tip 13 is received by the sleeve 40, as shown in FIG. 5B. When the tip end ridges 17 abut the sleeve tip end projections 54, a gap is formed between the sleeve interior surface 41 and the tip end portion 18. Thus, gas, fluid, and debris may freely flow into the sleeve 40, up towards the tip end portion 18, and into the tip end openings 16 and/or apertures 19.

Referring to FIGS. 4A and 4B, the sleeve 40 may include grooves or ridges along its external surface as desired to aid in attaching or removing the sleeve 40. Preferably, sleeve exterior surface 58 includes ridges 47 and 52 that extend longitudinally along the length of the sleeve 40 on both the upper and lower surfaces of the sleeve 40. Optimally, two center ridges 47 are formed proximally to one another along the center of both the upper and lower surfaces of the sleeve 40, wherein such center ridges 47 are disposed between two lateral ridges 52. The sleeve 40 may include additional ribs, ridges, and other projections as well as grooves and depressions on the sleeve exterior surface 58 to lend structural support and aid in conducting gases, fluids, and materials into the interior of the sleeve 40.

The sleeve 40 includes an elongate, nominally straight sleeve tubular body that defines an internal channel having an open, proximal sleeve end portion 43 and an enclosed distal tip sleeve end portion 45. The sleeve 40 also contains a plurality of spaced orifices 62 that allow gases, fluids, and materials to flow into the interior of the sleeve 40. The orifices 62 are preferably round or ovoid but other shapes may be used. The orifices 62 are sized to permit the inflow of gases, fluids, and materials of a size that will not clog the opening 16 in the neck member 14 when the neck member is enclosed by the sleeve 40. Larger materials, on the other hand, such as body tissue, are unable to pass through the orifices 62 and may clog them. Thus, it is preferred, but not essential, that the orifices 62 are formed between the center ridges 47 and the lateral ridges 52 on each side of the sleeve 40 so that the ridges 47 and 52 may engage the tissue and form a gap between the tissue and the orifices 62, thereby preventing clogging. The orifices 62 on one side of sleeve 40 are in alignment with orifices 62 on the opposite side of the sleeve.

The sleeve 40 is preferably constructed from a material suitably flexible to conform to the shape of an aspirator neck 14 member inserted therein. Suitable materials to construct the tapered neck include rigid or semi-rigid, resiliently deformable materials adaptable for use in the medical arts such as polymeric or resinous plastic. The sleeve 40 may instead be contoured to match the contours present in the neck member 14.

Referring back to FIG. 2, the male coupling member 26 includes an outside surface 28. The male coupling member 26 may be formed in the distal portion of the handle member 20 or attached to the handle member 20 as a separate component. Alternatively, the male coupling member 26 may be attached to the neck member 14 and not attached to the handle member 20. The male coupling member 26 is between about [40 and 55 mm] long in the longitudinal $\alpha'$ direction.

In one embodiment, the male coupling member 26 is generally tapered along its longitudinal axis $\alpha'$ so that the cross-sectional area of the proximal end is greater than the cross sectional area of the distal end. In alternate embodiments, the cross-sectional areas of the proximal and distal ends may be approximately equal. Along its lateral axis, the proximal end of the male coupling member 26 is between about [4 and 20 mm] and the distal end is between about [4 and 20 mm]. In addition, the proximal cross-sectional area of the male coupling member 26 is less than the cross-sectional area of the distal end of the grip member 22.

The cross-sectional shape of the male coupling member 26 may remain constant or vary (as depicted in FIG. 2) along the longitudinal axis $\alpha$. The male coupling member 26, excluding longitudinal exterior grooves 74 (described below), may have any cross-sectional shape, but preferably has a cross-sectional shape that is generally round, ovoid, square, rectangular, triangular, hexagonal, or other closed shape.

Still referring to FIG. 2, handle member 20 includes at least one longitudinal exterior groove 74 extending longitudinally along the outside surface of handle member 20. In one embodiment, longitudinal exterior grooves 74 extend from the proximal to the distal end of male coupling member 26, but it is appreciated that the grooves 74 may extend from the proximal end of the male coupling member 26 and along only a portion of the male coupling member 26. In addition, the longitudinal exterior grooves 74 extend onto a section of the grip member 22 from its distal end. Alternatively, separate grooves may be included in the grip member 22 that are in communication or intersect with longitudinal exterior grooves 74 on the male coupling member 26. Longitudinal exterior grooves 74 are between 1 and 7 mm deep and 1 and 10 mm wide, and have any cross-sectional shape such as U-shaped, V-shaped or other suitable groove shape.

Figure 14:
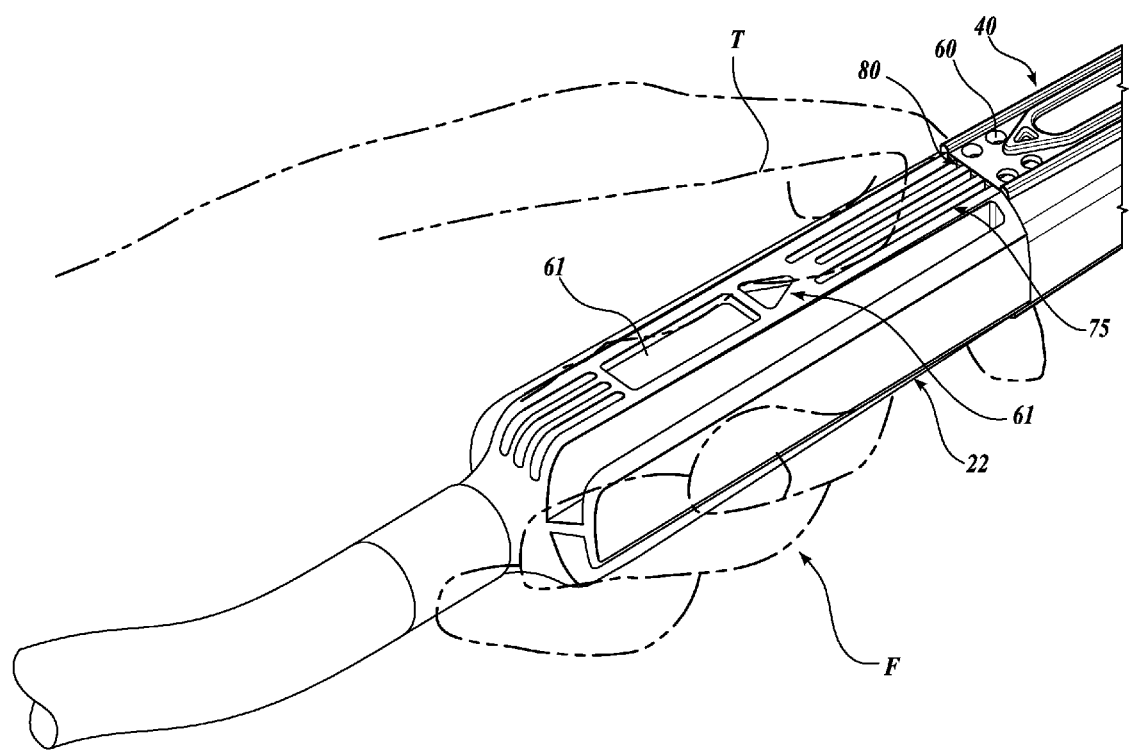
FIG. 14 is an isometric view of a user gripping a portion of a surgical aspirator tip, wherein a portion of the surgical aspirator tip is covered with the user's thumb.
Figure 15:
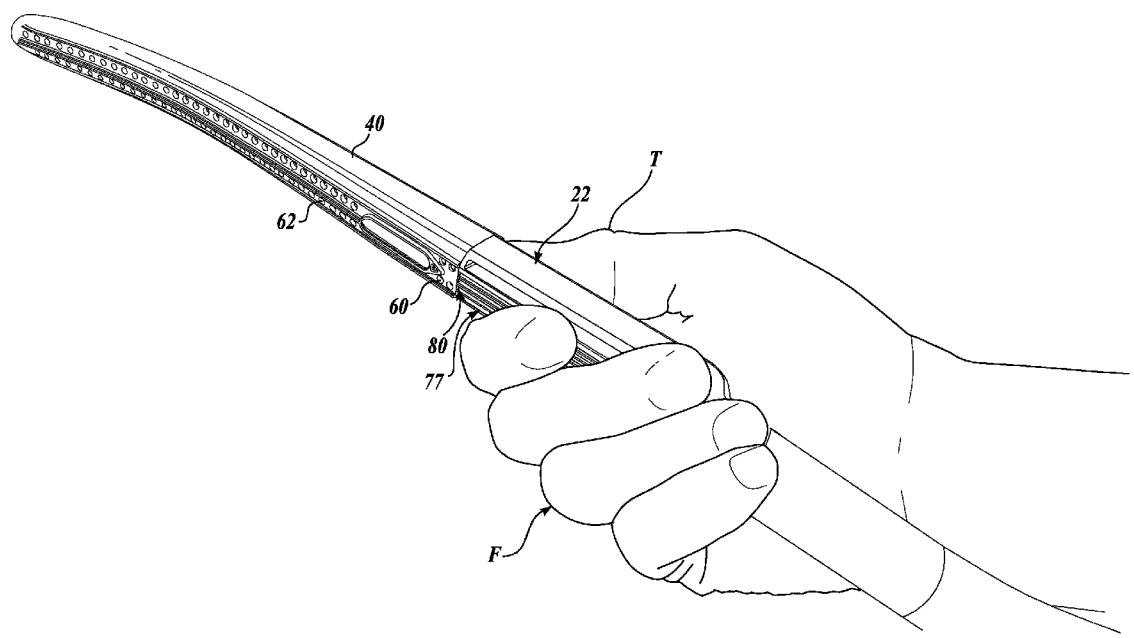
FIG. 15 is an isometric view of the user gripping a portion of a surgical aspirator tip, wherein a portion of the surgical aspirator tip is covered with the user's remaining fingers.

The longitudinal grooves 74 may extend along the entire length of the grip member 22, or may instead extend along only a portion of the grip member 22. Referring to FIGS. 14 and 15, a first set 75 of longitudinal grooves 74 are preferably formed along the top of the grip member 22 and a second set 77 of longitudinal grooves 74 are formed along the bottom of the grip member 22. Each set of longitudinal grooves 75 and 77 is shown having three longitudinal exterior grooves 74; however, fewer or more than three grooves 74 may instead be used. The first set 75 of longitudinal grooves preferably extend along only a portion of the grip member 22, and the second set 77 of longitudinal grooves preferably extend along the entire length of the grip member 22.

As can best be seen by referring to FIG. 2, the grip member 22 of the handle 20 may also include a lateral groove 76 formed along each side of the grip member 22 lateral to the longitudinal exterior grooves 74. The lateral grooves 76 may extend along substantially the entire length of the grip member 22 or only a portion thereof. The lateral grooves 76 provide traction on the grip member 22 to aid in holding the grip member, especially when attaching or removing the sleeve 40.

Still referring to FIG. 2, the grip member 22 is suitably sized to be received into an average sized hand but larger or smaller grip sections may be constructed for larger or smaller hands respectively. When being held in a typical manner by a user, the top side of the grip member 22 is engageable with a user's thumb T, and the bottom side of the grip member 22 is engageable with the remaining fingers F (see FIGS. 14 and 15). However, it should be appreciated that the grip member 22 may be held in any comfortable, effective manner. For instance, the user may instead wrap his entire hand around the grip member 22 such that his fingers F engage the top side of the grip member 22. Generally, the grip member 22 may be between about [35 and 80 mm] long and have a cross-sectional width between about [12 and 30 mm] and a cross-sectional height between about [12 and 30 mm]. The grip member 22 may also be tapered or include contours along its longitudinal axis for a more comfortable grip.

Referring back to FIG. 4A, the sleeve 40 includes an open, proximal aspirator sleeve end, or female coupling portion 42, and an enclosed, distal tip sleeve end portion 45. The female coupling member 42 includes a wall 46 with an internal surface 48 that defines an internal receiving volume V. The female coupling member 42 is generally tapered along its longitudinal axis $\alpha'$ so that the cross-sectional area of the proximal end is greater than the cross-sectional area of the distal end. In alternate embodiments, other profiles may be used such that the cross-sectional areas of the female coupling portion 42 and the distal section 45 of the sleeve 40 are approximately equal. In another embodiment, the female coupling portion 42 is tapered or contoured to approximate the taper or contour of the male coupling member 26. Along its lateral axis, the proximal end of the female coupling member 42 is between about [8 and 24 mm] and the distal end is between about [8 and 24 mm].

The cross-sectional shape of the female coupling member 42 of the sleeve 40 may remain constant or vary along the longitudinal axis $\alpha'$. The female coupling member 42 of the sleeve 40 may have any cross-sectional shape but is preferably generally round, ovoid, square, rectangular, triangular, hexagonal, or other closed shape. In an alternate embodiment, the cross-sectional shape of the female coupling portion 42 approximates the cross-sectional shape of the male coupling member 26.

Referring now to FIGS. 5A-5C, the sleeve 40 slides over the neck 14 of the tip 13 so that the neck 14 is completely encased by the sleeve 40. Generally, the sleeve 40 is attached to the tip 13 at the handle member 20 by a coupling device. The coupling device includes a tip coupling member such as the male coupling member 26, shown in FIG. 2, and a sleeve coupling member such as the female coupling member 42, shown in FIG. 4A. The male coupling member is received into the receiving volume V (see FIG. 4A) of the female coupling member 42. A coupled region 70 is formed where the male coupling member 26 is inserted into the female coupling member 42.

Referring again to FIG. 2, sleeve alignment grooves 56 may be formed on the male coupling member 26. The sleeve alignment grooves 56 are formed in the proximal end of the male coupling member 26, and extend a predetermined distance towards the distal end of the male coupling member 26. The sleeve alignment grooves 56 are formed on opposite sides of the male coupling member 26 on portions on the male coupling member outside surface 28 not covered by longitudinal exterior grooves 74. The sleeve alignment grooves 56 may have any cross-sectional shape, but preferably have a cross-sectional shape that is generally U-shaped, V-shaped, or other suitable groove shape.

Referring back to FIG. 4A, sleeve 40 may include sleeve alignment ribs 50 formed along a portion of the interior surface of the sleeve 41 in the space between the orifices 62. The sleeve alignment ribs 50 extend from the proximal end of the sleeve 43 towards the distal tip sleeve end portion 45. Preferably, two sleeve alignment ribs 50 are formed on the interior surface of the sleeve 41 on opposite sides of the sleeve 40. The sleeve alignment ribs 50 taper in height as the ribs 50 extend toward the distal tip sleeve end portion 45. The sleeve alignment ribs 50 substantially conform to the shape of the sleeve alignment grooves 56, such that the sleeve alignment grooves 56 may closely, slidably receive the sleeve alignment ribs 50 when the sleeve 40 receives the tip 13, as shown in FIG. 5C. The sleeve alignment ribs 50 are tapered at the proximal end of the sleeve to form lead-in portions 49. The lead-in portions 49 aid in securing the sleeve 40 to the tip 13 by guiding the sleeve alignment ribs 50 into the sleeve alignment grooves 56.

The sleeve alignment ribs 50 are slidably received by the sleeve alignment grooves 56 so that the sleeve 40 is properly aligned and coupled to the tip 13. When properly mated, the tip end projections 54 abut the four tip end ridges 17 to form a gap between the tip end portion 18 and the sleeve 40, as shown in FIG. 5B. Additionally, cross-holes 60 remain properly aligned with longitudinal exterior grooves 74 (as described) to ensure proper venting and air flow into the sleeve 40. Moreover, when the ribs 50 are slidably received by the grooves 56, the sleeve 40 is locked into place and will not rotate about tip 13. Thus, while the tip 13 is being used, the tip end projections 54 will remain abutted to the four tip end ridges 17, and the cross-holes 60 will remain properly aligned with longitudinal exterior grooves 74.

To further aid in proper alignment, indicator designs or indicia 59 and 61 may be formed on the sleeve 40 and handle member 20, respectively. Preferably, the indicator designs 59 and 61 comprise an arrow or other suitable design or indicia. The indicator design 59 is in alignment with the center ridges 47 of the sleeve 40 and is in the form of an arrow, with the arrow pointing towards the proximal end of the sleeve 40. The indicator design 59 is formed on both sides of the sleeve 40. A similar indicator design 61 is formed on the top of the grip member 22 in alignment with the first set of longitudinal exterior grooves 75, with the arrow pointing towards the male coupling member 26. Either of the two arrows 59 on the sleeve 40 may be aligned with the arrow 61 on the grip member 22 when inserting the tip 13 into the sleeve 40, such that the sleeve may be rotated 180° and still properly mate with the tip. The indicator designs 59 and 61 will facilitate proper alignment of the sleeve alignment ribs 50 with the sleeve alignment grooves 56, thereby ensuring that the tip end projections 54 abut the four tip end ridges 17. It should be appreciated that any suitable design or indicia may be used to guide the insertion of the tip 13 into the sleeve 40. The indicator design 61 is formed in alignment with the first set 75 of longitudinal grooves 74 on the top of the grip member 22 such that the first set 75 of longitudinal grooves extends only partially along the grip member 22 from the distal end of the grip member 22. It should be appreciated that the indicator design 61 may instead be formed within the first set of longitudinal grooves 75 such that the continuity of the longitudinal grooves 75 is not interrupted, and the grooves 75 instead extend along substantially the entire length of the grip member 22.

Figure 6:
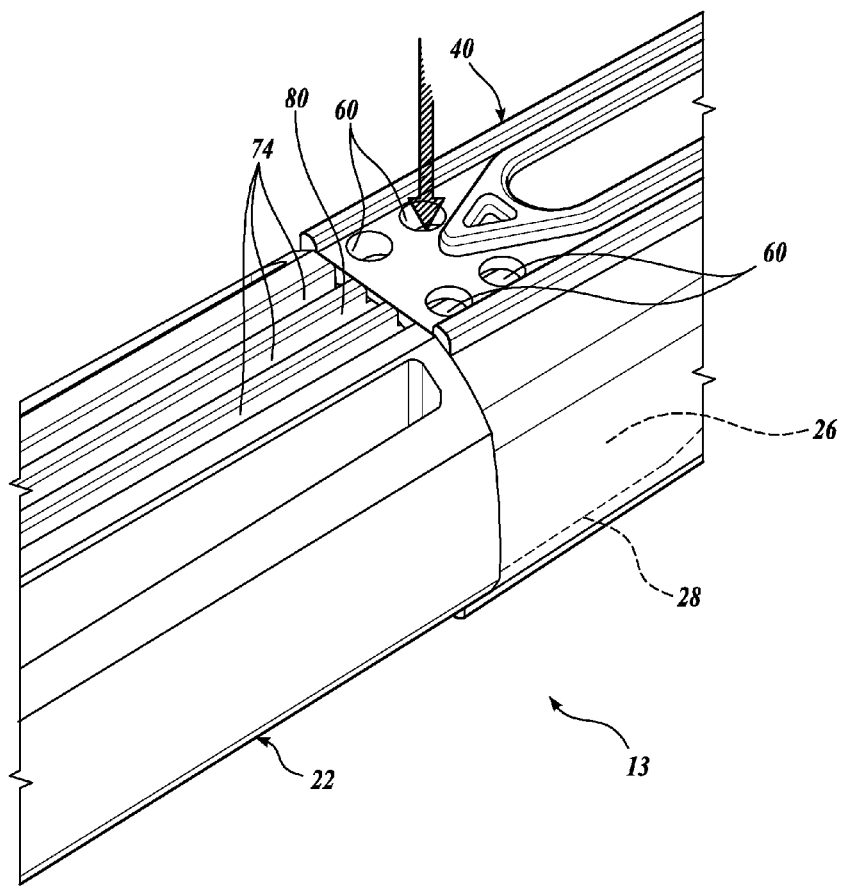
FIG. 6 is a side perspective view of male coupling member joined to a female coupling member to form a coupled region of a surgical aspirator tip and sleeve combination.
Figure 7B:
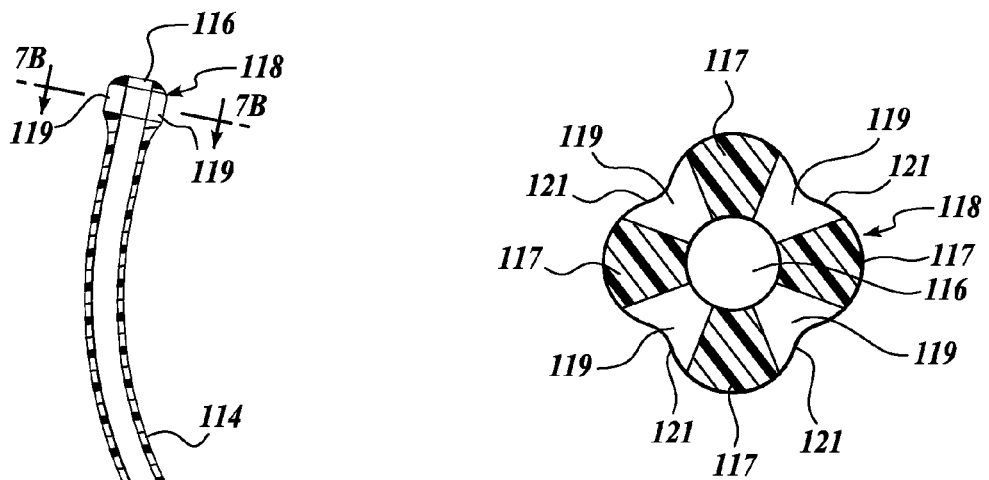
FIG. 7B is a cross-section view of a surgical aspirator tip end of the surgical aspirator tip of FIG. 7A, taken across 7B-7B.
Figure 7A:
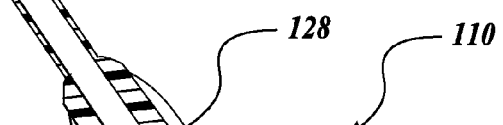
FIG. 7A is a longitudinal cross-section view of an alternate embodiment of a surgical aspirator tip.
Figure 7C:
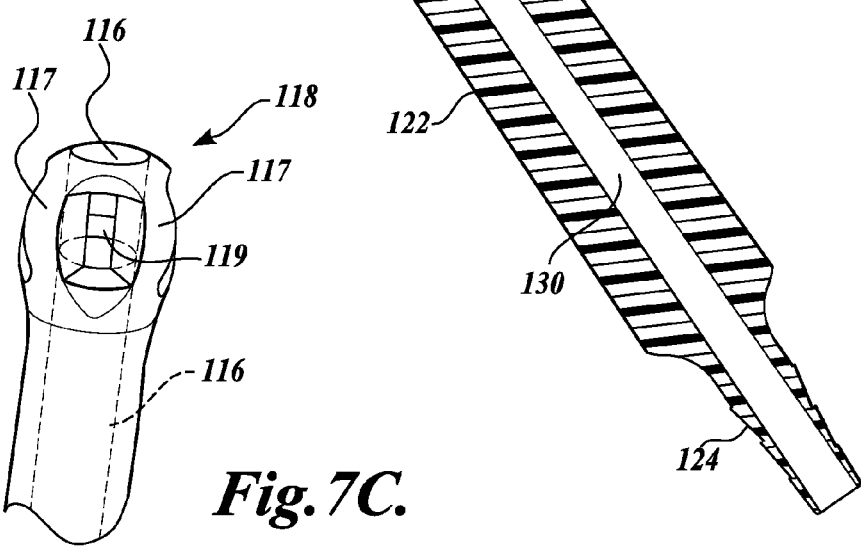
FIG. 7C is a side perspective view of the surgical aspirator tip end of FIG. 7A.

Now referring to FIG. 6, the internal surface 48 of the wall 46 of the female coupling member 42 contacts the outside surface 28 of the male coupling member 26 along the coupled region 70. Portions of the internal surface 48 of the female coupling member 42 do not contact the outside surface 28 of the male coupling member 26. Particularly, the sections of the internal surface 48 of the female coupling member 42 adjacent to longitudinal exterior grooves 74 do not contact the outside surface 28 of male coupling member 26. Consequently, venting channels 80 are formed between the internal surface 48 of the wall 46 and the outside surface 28 of the male coupling member 26 as depicted in FIG. 6. These venting channels 80 allow air to flow between the external environment into the interior of the sleeve 40. Each individual venting channel is in communication with other venting channels, the external environment, and/or the interior of the sleeve 40 as required to provide communication between the external environment and the interior of the sleeve 40.

In one embodiment depicted in FIGS. 5A and 6, the distal end of the grip member 22 abuts the proximal end of the female coupling member 42. As mentioned above, longitudinal exterior grooves 74 extend onto grip member 22 from the distal end. Air flows through the portion of longitudinal exterior grooves 74 located in handle member 22 into the venting channels 80. This configuration may prevent both the hands of the user and the distal end of the grip member 22 from interfering with the air flow through the venting channels 80.

With the sleeve 40 in place, the distal end of the tip 13 and sleeve 40 combination may be inserted into the wound, surgical site, or bodily orifice to remove fluids therein. Suction flows from the suction source, such as a suction pump, through the tube 38 and into the handle member 20 (as shown in FIG. 1). As shown in FIG. 2, the tube coupling member 24 may include a tiered section that is coupled to the tube 38 (see FIG. 1) by inserting one or more of the tiers having a smaller cross-sectional area into the tube 38, however, any tube coupling mechanism may be used. The tube 38 may be constructed from any tubular material suitable for transmitting suction forces to a surgical aspirator and gases, fluids and materials from a surgical site known in the medical arts.

Suction traverses the handle member 20 and into the neck member 14. Suction travels up the neck and pulls gases, fluids, and small materials into the opening 16. The gases, fluids, and materials inside the sleeve 40 flow from the wound, surgical site, or bodily orifice into the sleeve 40 through the plurality of orifices 62 and opening 16. If the orifices 62 become clogged such that the flow of gases, fluids, and materials into the interior of the sleeve 40 is restricted, air flow is available to the sleeve through the venting channels 80. Air provided by the venting channels may prevent uneven distribution of suction forces over any unclogged orifices 62. Otherwise, the suction force is concentrated over too few orifices 62, the tissue surrounding the wound, surgical site, or orifice could be pulled into the orifices 62 in the sleeve 40 possibly causing discomfort, pain, and injury to the patient.

Referring to FIG. 6, cross-holes 60 may be formed in the portion of the wall 46 between the venting channels 80 and the external environment to provide another means by which air may enter the venting channels 80. Because the handle 20 is not generally in contact with the tissue or fluids at the surgical site, the portion of longitudinal exterior grooves 74 located in the handle member 22 and cross-holes 60 in the sleeve 40 are unlikely to become clogged with tissue. Therefore, a constant airflow is available inside the sleeve 40 and particularly in the area surrounding opening 16 in the tip 13. This airflow prevents uneven distribution of suction to the holes of the sleeve 40.

Referring to FIGS. 14 and 15, the level of suction within the sleeve 40 can be varied by covering at least a portion of the longitudinal exterior grooves 74 on the grip member 22. Air flows through the longitudinal exterior grooves 74 into the venting channels 80 and thereafter into the interior of the sleeve 40 to prevent uneven distribution of suction within the sleeve 40 at the orifices 62. When a portion of the longitudinal exterior grooves 74 is covered, the air entering the venting channels 80 is reduced, thereby adjusting the level of suction within the interior of the sleeve 40. The longitudinal exterior grooves 74 can be covered in any effective manner with a portion of a user's hand.

Referring to FIG. 14, the first set 75 of longitudinal grooves 74 may be covered at least partially with a user's thumb T to reduce the effective lengths of the longitudinal grooves 74, thus reducing the air flow into the venting channels 80. With less air entering the sleeve 40 through the venting channels 80, the suction within the interior of the sleeve 40 is increased. To decrease the suction within the sleeve 40, the thumb T can be moved rearwardly along the grip member 22 such that a greater portion of the first set 75 of longitudinal grooves 74 is exposed to the environment, thereby allowing more air to flow through the venting channels 80 into the sleeve 40.

Referring to FIG. 15, the suction within the sleeve 40 can also be adjusted by covering a portion of the second set 77 of longitudinal grooves 74. Preferably, the grip member 22 is adapted to be held by the user such that the user's remaining fingers F can cover at least a portion of the second set 77 of longitudinal grooves 74 when the thumb T is engaging the first set of second set of longitudinal grooves 75.

It should be appreciated that the longitudinal grooves 74 may instead be covered with other portions of the hand. For instance, the user may wrap his or her hand around the grip member 22 such that the palm of the hand engages the second set 77 of longitudinal grooves 74 and the user's fingers F engage the first set 75 of longitudinal grooves 74. Moreover, the suction may be varied by using an adjustable sleeve or other mechanism (not shown) that is couplable to the grip member 22 and is adapted to cover at least a portion of the longitudinal grooves 74 of sets 75 and/or 77.

The user adjusts the position of his or her hand as various levels of suction are needed. When the aspirator tip 13 and sleeve 40 are deep within a patient's body such that a majority of the orifices 62 and the cross-holes 60 are covered by a portion of the patient's body, air flow into the sleeve 40 is decreased. This may also occur if some of the orifices 62 and/or cross-holes 60 becomes clogged. Without sufficient venting into the sleeve 40, the suction level within the interior of the sleeve 40 increases, and the tissues collapse around the aspirator tip and sleeve. To relieve some of the pressure within the sleeve 40, the user can hold the grip member 22 so as to cover only a minimal portion of the longitudinal grooves 74 of sets 75 and 77, thereby allowing air to flow into the sleeve 40 and relieve some of the pressure on the tissue.

If, on the other hand, the aspirator tip 13 and sleeve 40 is only partially enclosed within the patient's body such that a majority of the orifices 62 and the cross-holes 60 are exposed to the atmosphere, air can flow freely into the sleeve 40 to relieve the pressure within the sleeve 40. As such, the suction level within the interior of the sleeve 40 may decrease below an optimal level. To increase the suction within the sleeve 40, the longitudinal grooves 74 of sets 75 and/or 77 can be increasingly covered by the user's hand until the desired level of suction is attained.

The tip 13 may be used without the sleeve 40 to accurately and efficiently drain fluids from a specific area, such as a surgical site. Accurate and effective draining is necessary because even a small amount of fluid or film can obstruct a medical operator's view. When placing the tip end portion 18 within a body cavity, the tip end ridges 17 bridge the adjacent soft tissue and maintain the channels open in the grooves 21. Thus, if the tip end opening 16 is clogged, fluid, gas, and materials may flow into the channels defined by grooves 21 and into the openings 19. If the tip 13 is placed within a cavity so that is oriented substantially orthogonally to a tissue wall, the tip end opening 16, as well as the openings 19 adjacent the end opening, may be clogged with tissue. In this case, the fluid, gas, and materials may flow into the channels defined by grooves 21 and into the uncovered openings 19 located father away form the opening 16.

As a non-limiting example, the tip 13 of the present invention may be formed by injection molding. For illustrative purposes, one non-limiting example of a method by which the tip 13 may be constructed will be provided herein.

A tip mold is first formed to produce a complete tip 13 during the molding process. The tip guard mold includes an upper and lower portion, and each portion of the tip guard mold contains a portion of a mold cavity. The upper and lower portions contain a mold for the upper half of the tip 13 and the lower half of the tip 13. Further, the mold includes inwardly extending projections that extend into the mold cavity to form additional openings and grooves in the tip 13.

Both portions of the tip guard mold are coupled together to define the mold cavity therebetween. At least one inlet channel is included in the mold to allow the inflow of material into the mold cavity. An injection nozzle injects material through the inlet channel and into the mold cavity. The injected material fills the mold cavity and surrounds a section of the tip guard core.

While one method of forming the tip is depicted in this application, it is apparent to one of ordinary skill in the art that alternate equivalent methods are available. For example, both the handle member 20 and the tubular neck member 14 could be molded separately and then secured together with a fluid tight seal.

Referring now to FIGS. 7-12, an alternate embodiment of the present invention is depicted, wherein like numerals are used for like parts relative to FIGS. 1-6. Referring first to FIG. 7A-7C, the tip end portion 118 contains tip end projections 117 that extend transversely from the tip end portion 118, as shown in FIG. 7C. The tip end projections 117 are used to secure the tip end portion 118 of the tip 110 within the distal end of the sleeve 140. Preferably, the tip end portion 118 contains four tip end projections 117 that are generally the same size and shape and equidistant from one another. Alternatively, two symmetrical tip end projections 117 with two tip end grooves 121 may be used. The tip end portion 118 includes additional tip end orifices 119 located circumferentially about tip end portion 118, which extend from the exterior surface of the tip end portion 118 radially through the tip end portion 118 intersecting the tip end opening 116, as shown in FIG. 7B. The tip end orifices 119 are preferably disposed between the tip end projections 117. Therefore, four tip end orifices 119 may be formed, but it may be appreciated that greater or less than four tip end orifices 119 may be included.

Figure 8:
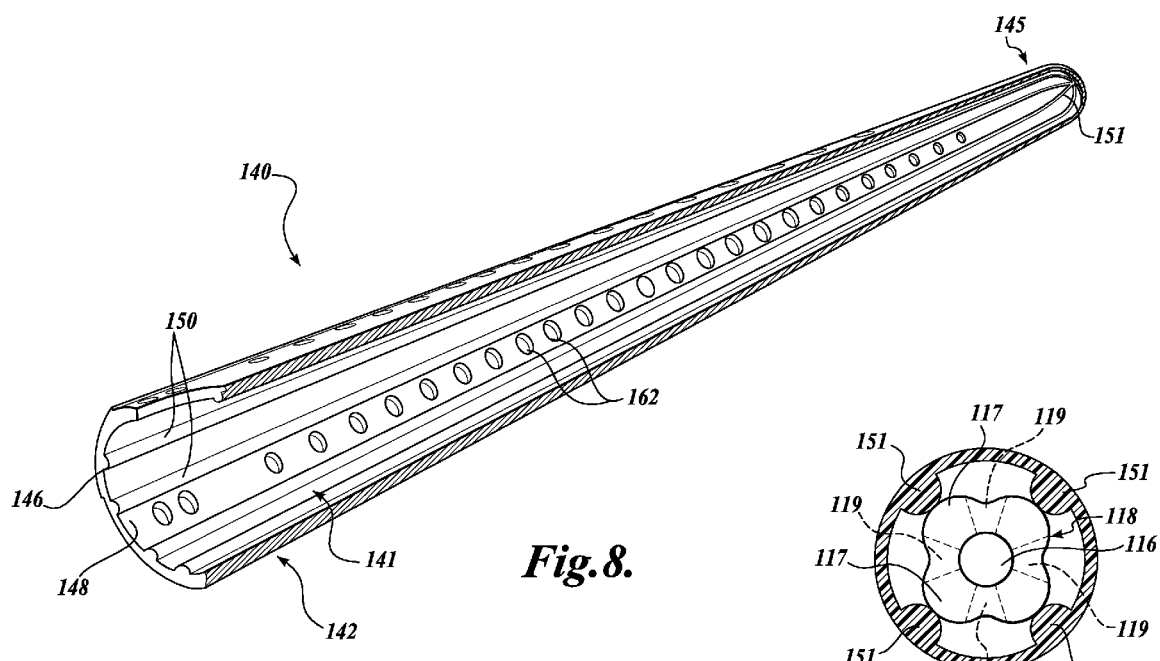
FIG. 8 is a side perspective view of an alternate embodiment of a surgical aspirator sleeve, where the sleeve is cut away to show the interior pairs of converging longitudinal grooved ribs.

Referring now to FIG. 8, a sleeve 140 includes at least two pairs of converging longitudinal grooved ribs 150 on the interior surface 141 of the sleeve 140. The pairs of grooved ribs 150 originate at the proximal end of the sleeve 140 and converge near the distal tip sleeve end portion 145 of the sleeve 140 to form a converged rib end 151. In another embodiment, the grooved ribs 150 may originate at the distal end of the female coupling member 142 and converge near the distal tip sleeve end portion 145. The sleeve 140 is shown as having four pairs of converging longitudinal grooved ribs 150 on the interior surface 141 of the sleeve 140. Each pair of converging longitudinal grooved ribs 150 are spaced generally equidistant from the other grooved ribs 150.

The converging longitudinal grooved ribs 150 protrude from the interior surface 141 of the sleeve 140 such that the ribs 150 may contact the tubular neck member 114 of the tip 110 where the sleeve 40 has flexibly conformed to the shape of the neck 114. Thus, where the neck member 114 is bent, the sleeve 140 engages the neck 114 when the sleeve 140 bends to generally conform to the shape of the neck 114. In those areas, the ribs 150 may engage the neck 114 to maintain a gap between the neck 114 and the sleeve 140 and to allow the passage of fluids and other debris.

Figure 9:
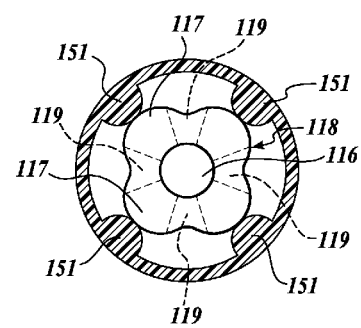
FIG. 9 is a cross-section view of the surgical aspirator tip end shown in FIG. 7A, wherein the tip end has engaged the converging grooved rib ends at the distal end of the aspirator sleeve.

Referring to FIG. 9, the tip end projections 117 on the tip end portion 118 engage the converged rib ends 151 at the distal tip sleeve end portion 145 when the neck member 114 is inserted into the sleeve 140. The converged rib ends 151 abut the tip end projections 117, forming a predetermined gap between the interior of the distal tip sleeve end portion 145 and the tip end portion 118. This gap may enable gas, fluids, and other debris to flow more freely into the tip end orifices 119 and the tip end opening 116 after entering the sleeve 140.

Figure 10:
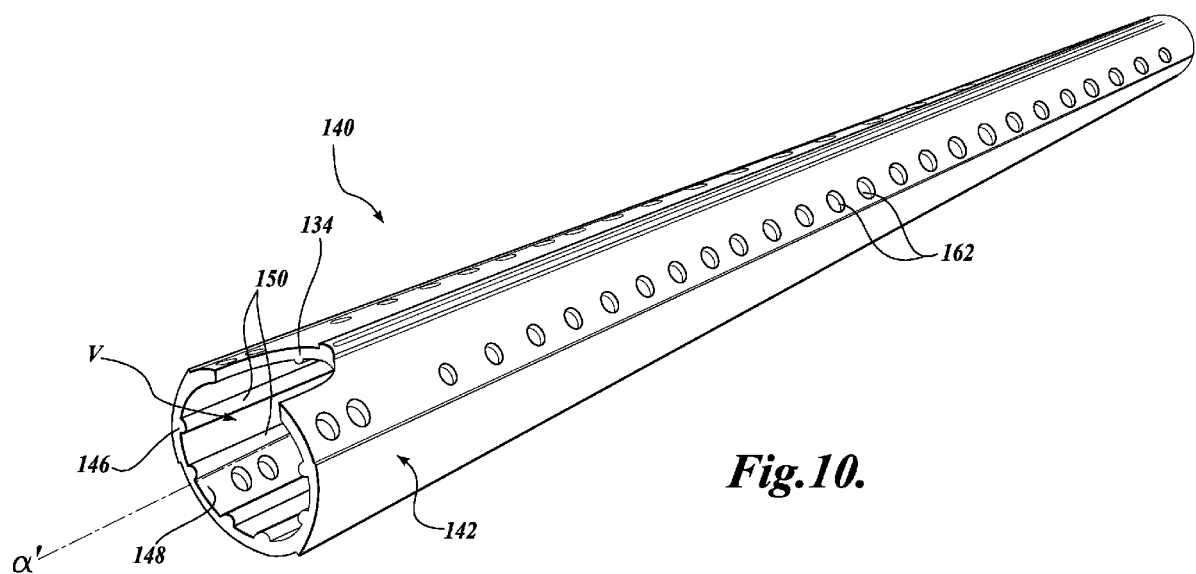
FIG. 10 is a side perspective view of an alternate embodiment of the sleeve.

Referring to FIGS. 10-13, a key and slot joint 131 is used to secure the coupled region 170. A slot 134 is formed in the proximal portion of the female coupling member 142, as shown in FIG. 10. The slot 134 is preferably U-shaped; however, other shapes may also be used. Moreover, the slot 134 is preferably formed in only a portion of the female coupling member 142. In other words, the slot 134 preferably does not extend from the proximal portion of the female coupling member 142 to the distal portion of the female coupling member 142. However, in alternate embodiments, the slot 134 may extend along the entire length of the female coupling member 142.

Figure 11:
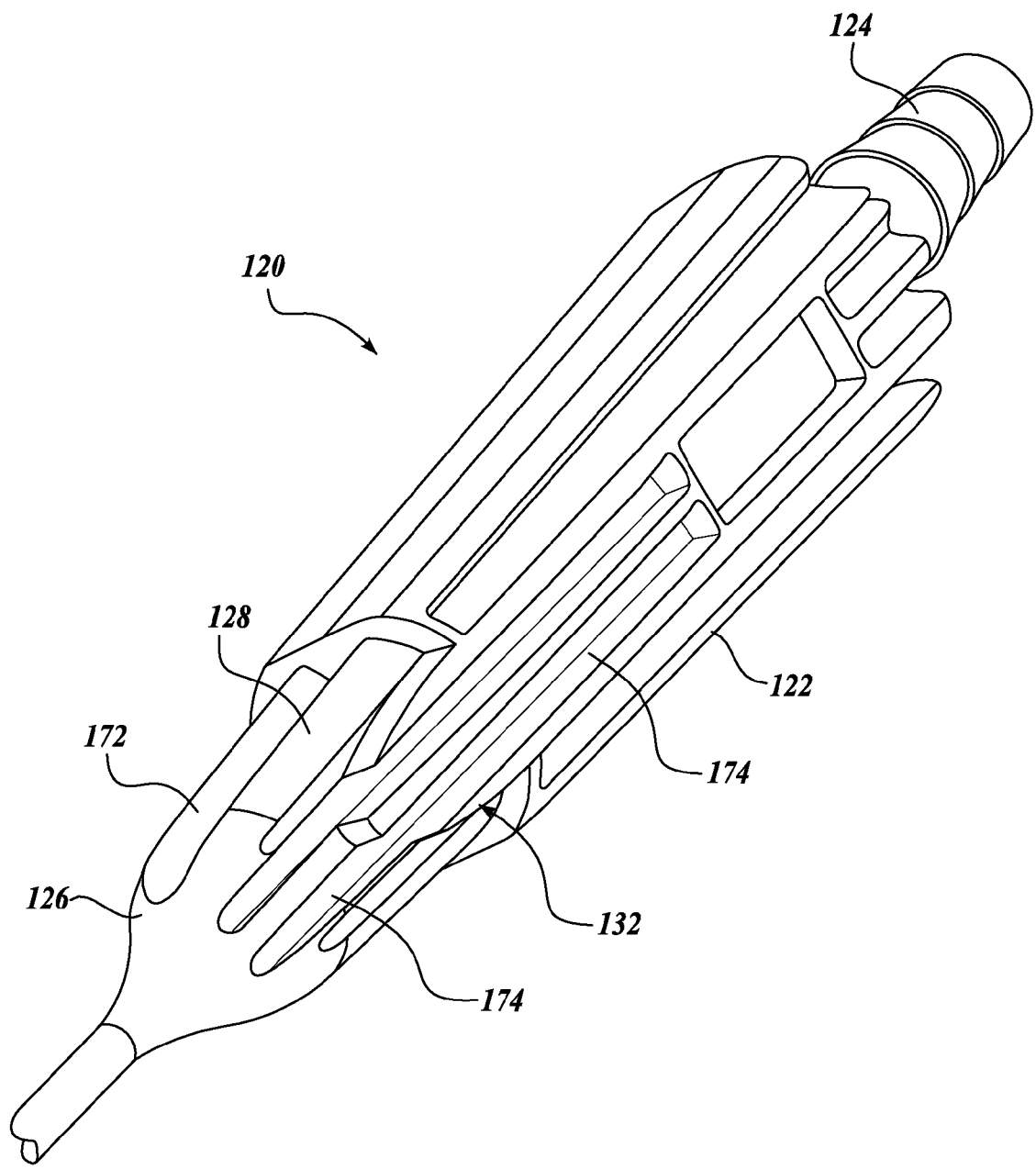
FIG. 11 is a side perspective view of an alternate embodiment of a male coupling member and grip member of a surgical aspirator tip.
Figure 12:
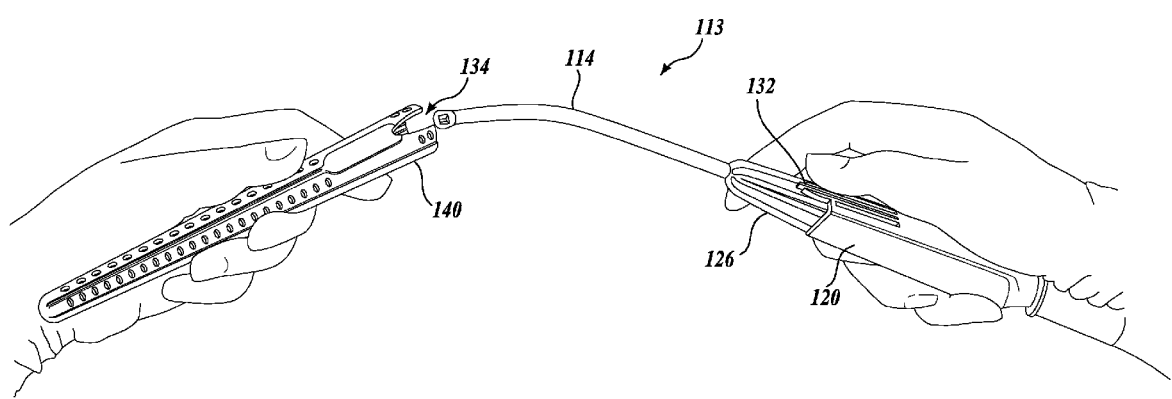
FIG. 12 is a side elevational view of a surgical aspirator tip and a surgical aspirator sleeve.
Figure 13:
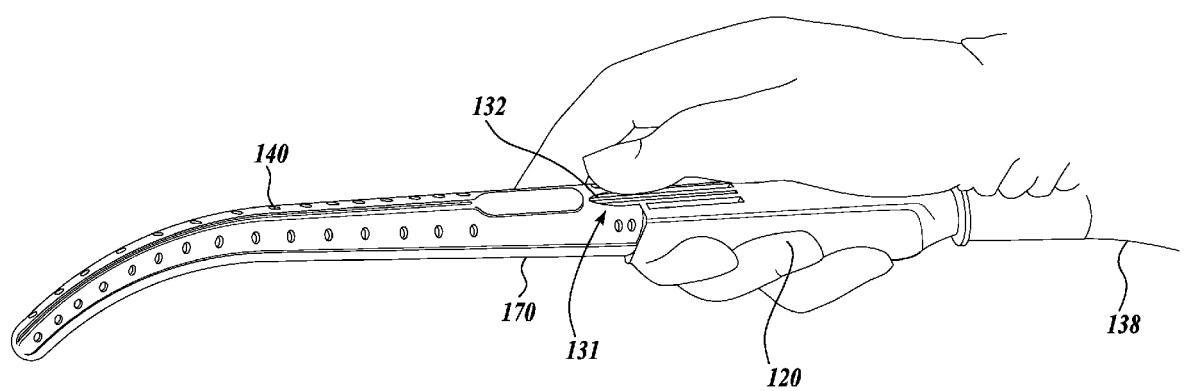
FIG. 13 is a side elevational view of a surgical aspirator tip joined with a surgical aspirator sleeve.

A key 132 is formed near the proximal portion of the male coupling member 126 on the male coupling member outside surface 128, as shown in FIG. 11. The longitudinal exterior grooves 174 may still be formed on the section of the male coupling member 126 where the key 132 is formed. In the alternative, the longitudinal exterior grooves 174 may not be formed on the key 132, such that the key 132 is solid. The key 132 is sized and shaped to generally conform to the size and shape of the slot 134. The key 132 protrudes from the male coupling member outside surface 128, such that the thickness of the key 132 is equal to or slightly greater than the thickness of the sleeve 140. Thus, when the male coupling member 126 is received into the female coupling member 142, as depicted in FIGS. 12 and 13, the slot 134 receives the key 132 to form the key and slot joint 131. The key and slot joint 31 ensures a proper fit between the male coupling member 126 and the female coupling member 142, such that the tip end projections 117 on the tip end portion 118 engage the converged rib ends 151 at the distal tip sleeve end portion 145 when the neck member 114 is inserted into the sleeve 140. In addition, the key and slot joint properly aligns the sleeve 140 with the tip 113 so that sleeve orifices 162 remain adjacent the longitudinal grooves 174 to ensure proper venting and air flow into the sleeve 140. The key and slot joint 131 may also lock the sleeve 140 into its position on the tip 113 and prevent the rotational movement of the female coupling member 142 relative to the male coupling member 126.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A surgical aspirator tip and sleeve combination, comprising:
   (a) a surgical aspirator tip having a hollow interior that is adapted to be placed into communication with a suction source, the surgical aspirator tip having a grip portion with a thickness, a coupling portion extending distally from the grip portion, the coupling portion having a thickness, and a neck portion extending distally from the coupling portion;
   (b) a surgical aspirator sleeve slidably receivable at least partially on the coupling portion to define an internal channel between the interior of the aspirator sleeve and the exterior of the neck portion of the surgical aspirator tip, wherein the internal channel is in fluid communication with the hollow interior of the aspirator tip, and wherein the aspirator sleeve includes a plurality of spaced orifices that provide fluid communication between the external environment and the internal channel;
   (c) at least one longitudinal groove formed at least partially along the grip portion and the coupling portion, the portion of the at least one longitudinal groove formed along the grip portion of a depth less than the thickness of the grip portion and the portion of the at least one longitudinal groove formed along the coupling portion of a depth less than the thickness of the coupling portion, wherein the longitudinal groove defines a venting channel in communication with the internal channel and the external environment, and wherein the at least one longitudinal groove is adapted to be at least partially covered to adjust the suction within the internal channel.

2. The sleeve and aspirator tip combination of claim 1, wherein the at least one longitudinal groove is coverable by a portion of a user's hand.

3. The sleeve and aspirator tip combination of claim 1, wherein the grip portion includes a top and a bottom, and wherein a first set of longitudinal grooves extend at least partially along the top of the grip portion.

4. The sleeve and aspirator tip combination of claim 3, wherein the first set of longitudinal grooves are adapted to be covered at least in part by a user's thumb.

5. The sleeve and aspirator tip combination of claim 4, wherein a second set of longitudinal grooves extends at least partially along the bottom of the grip portion.

6. The sleeve and aspirator tip combination of claim 5, wherein the second set of longitudinal grooves extend along substantially the entire length of the grip portion.

7. The sleeve and aspirator tip combination of claim 6, wherein the second set of longitudinal grooves are adapted to be covered at least in part by the user's remaining fingers.

8. A method of adjusting the suction in a sleeve and aspirator tip combination, the method comprising:
   (a) providing a surgical aspirator tip having a hollow interior, the surgical aspirator tip including a grip portion with a thickness, a coupling portion extending distally from the grip portion, the coupling portion having a thickness, and a neck portion extending distally from the coupling portion, wherein at least one longitudinal groove extends at least partially along the grip portion and the coupling portion to define at least one venting channel in fluid communication with the external environment, the portion of the at least one longitudinal groove formed along the grip portion of a depth less than the thickness of the grip portion and the portion of the at least one longitudinal groove formed along the coupling portion of a depth less than the thickness of the coupling portion;
   (b) disposing a surgical aspirator sleeve at least partially over the coupling portion of the surgical aspirator tip such that an internal channel is defined between the interior of the aspirator sleeve and the exterior of the neck portion of the surgical aspirator tip, wherein the internal channel is in fluid communication with both the hollow interior of the aspirator tip and the venting channel, wherein the aspirator sleeve includes a plurality of spaced orifices that provide fluid communication between the external environment and the internal channel;
   (c) placing the aspirator tip into communication with a suction source; and
   (d) varying the suction within the internal channel by covering at least a portion of the at least one longitudinal groove.

9. The method of claim 8, wherein the suction is varied by covering at least a portion of the at least one longitudinal groove with a user's hand.

10. The method of claim 8, wherein the grip portion includes a top and a bottom, and wherein a first set of longitudinal grooves extend at least partially along the top of the grip portion.

11. The method of claim 10, wherein the suction is varied by covering at least a portion of the first set of longitudinal grooves with a user's thumb.

12. The method of claim 11, wherein a second set of longitudinal grooves extend at least partially along the bottom of the grip portion.

13. The method of claim 12, wherein the second set of longitudinal grooves extend along substantially the entire length of the grip portion.

14. The method of claim 13, wherein the suction is varied by covering at least a portion of the second set of longitudinal grooves with the user's remaining fingers.

* * * * *